(12) United States Patent
Reinstorff

(10) Patent No.: US 8,590,558 B2
(45) Date of Patent: Nov. 26, 2013

(54) VALVE SYSTEM FOR A FLUID CHANNEL

(75) Inventor: Henning Reinstorff, Hamburg (DE)

(73) Assignee: Air Liquide Sante (International), Paris (FR)

( * ) Notice: Subject to any disclaimer, the term of this patent is extended or adjusted under 35 U.S.C. 154(b) by 221 days.

(21) Appl. No.: 13/059,308

(22) PCT Filed: Sep. 21, 2009

(86) PCT No.: PCT/EP2009/062178
§ 371 (c)(1),
(2), (4) Date: Feb. 16, 2011

(87) PCT Pub. No.: WO2010/034683
PCT Pub. Date: Apr. 1, 2010

(65) Prior Publication Data
US 2011/0132468 A1    Jun. 9, 2011

(30) Foreign Application Priority Data
Sep. 23, 2008    (DE) .................. 10 2008 048 501

(51) Int. Cl.
*F16K 17/36* (2006.01)
(52) U.S. Cl.
USPC ............................. 137/45; 137/43
(58) Field of Classification Search
USPC ................................. 137/38, 43, 45
See application file for complete search history.

(56) References Cited

U.S. PATENT DOCUMENTS

| | | | | |
|---|---|---|---|---|
| 799,454 A | * | 9/1905 | Cordner | 137/43 |
| 2,324,999 A | * | 7/1943 | Shinn | 137/43 |
| 2,954,904 A | | 10/1960 | Potoczky | |
| 4,690,375 A | | 9/1987 | Vorhis | |
| 5,505,345 A | | 4/1996 | Zeid | |
| 5,894,966 A | * | 4/1999 | Bobey et al. | 137/38 |

FOREIGN PATENT DOCUMENTS

| | | |
|---|---|---|
| CH | 276994 | 11/1951 |
| DE | 3013581 A1 | 1/1981 |
| EP | 1772392 A2 | 4/2007 |
| FR | 1529535 A | 6/1968 |
| FR | 2835812 A1 | 8/2003 |
| GB | 2001933 A | 2/1979 |

OTHER PUBLICATIONS

International Search Report, dated Feb. 24, 2010, from corresponding PCT application.
German Search Report, Dated Aug. 12, 2009, in 102008048501.2-12.

* cited by examiner

*Primary Examiner* — Kevin Lee
(74) *Attorney, Agent, or Firm* — Young & Thompson

(57) ABSTRACT

A valve system (5) connectable to a fluid channel (3), wherein the valve system (5) includes an actuating element (33) and a closing element (17) for selectively closing and opening of the channel (3), wherein the valve system (5) includes a chamber (15) and a movable coupling member (37), wherein at least one section (48) of the coupling member (37) is located within the chamber (15) and the coupling member (37) is capable of moving under its gravitational force into a transfer position in which the coupling member (37) may transfer to the closing element (17) an external force acting on the actuating element (33) towards the closing element (17).

20 Claims, 13 Drawing Sheets

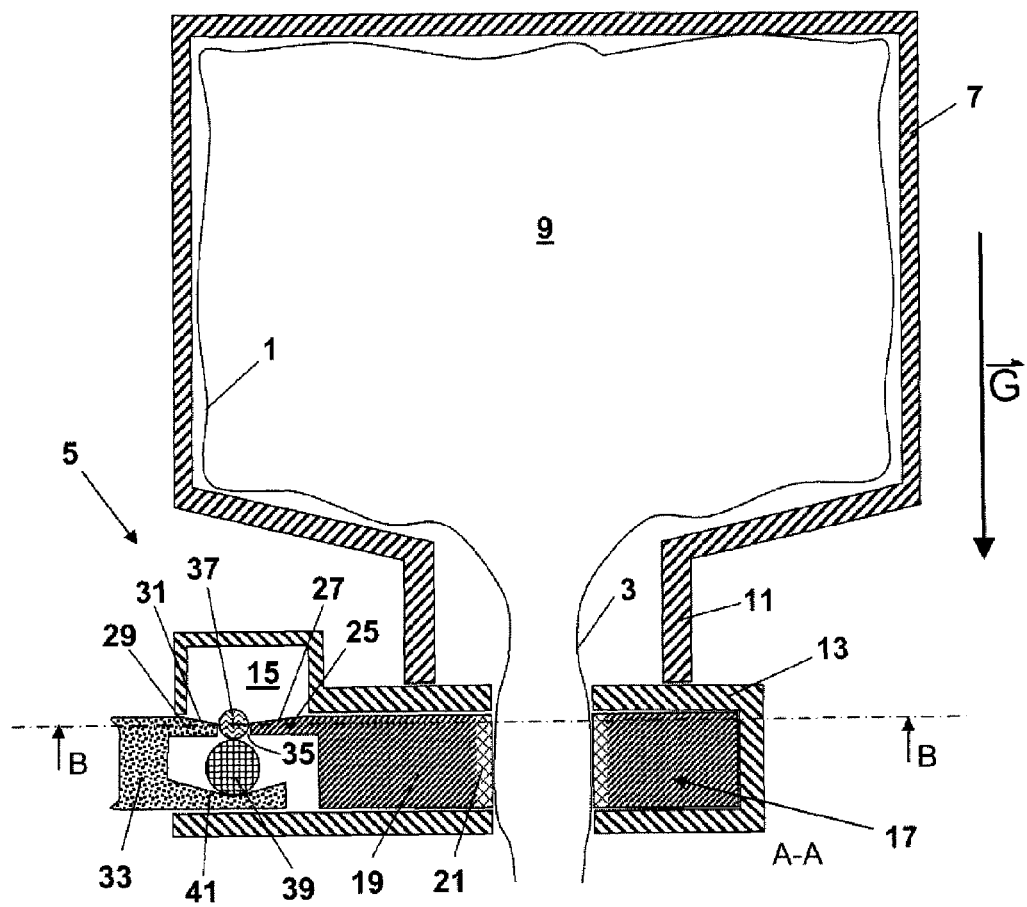
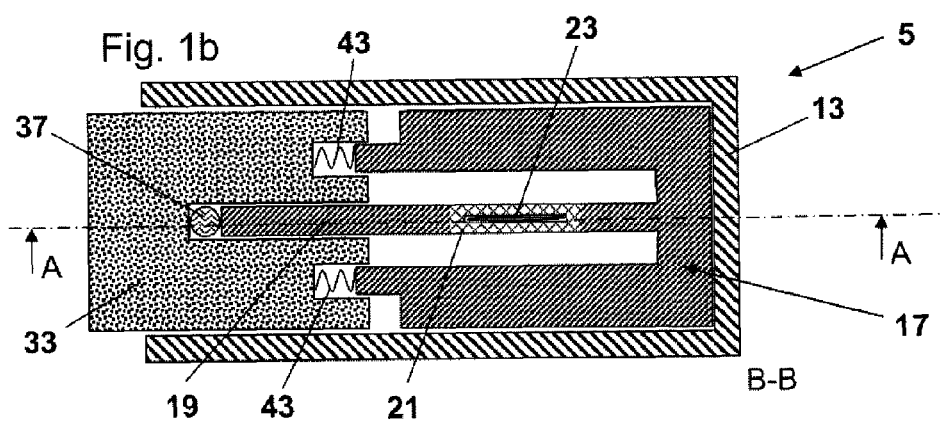

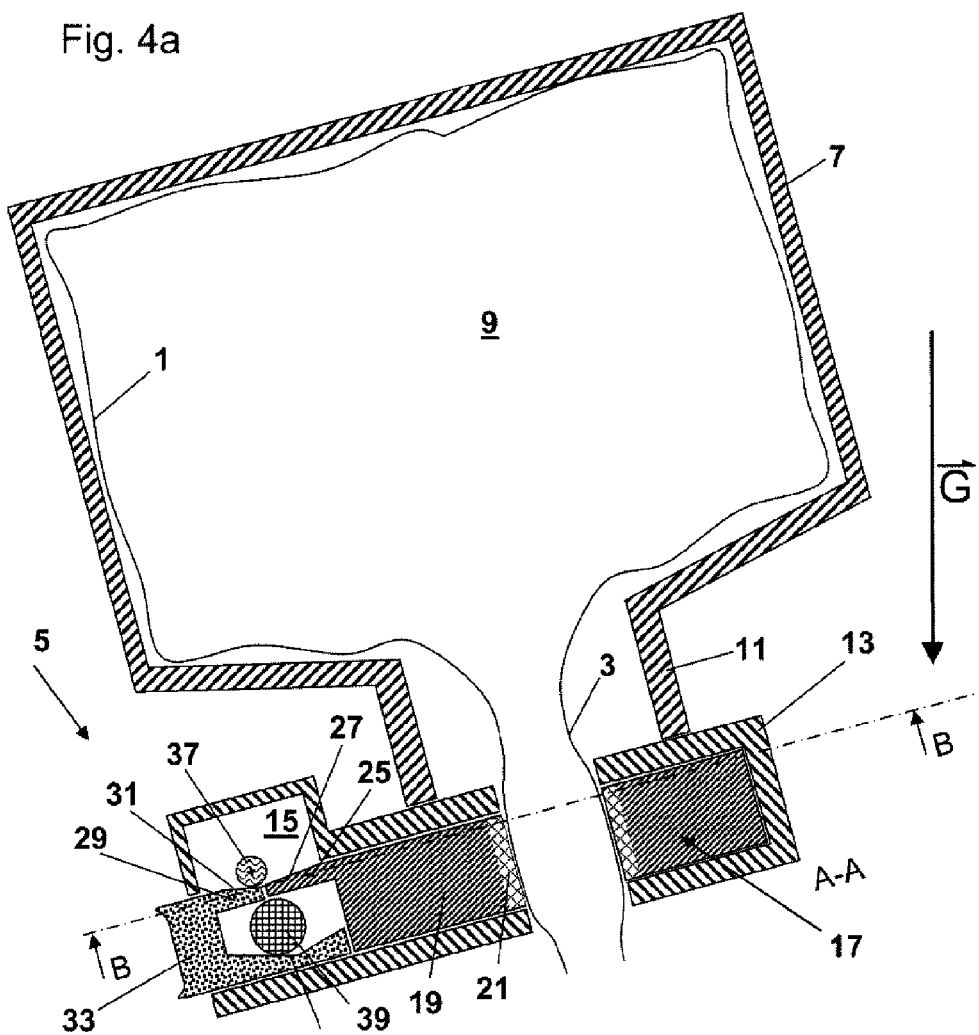
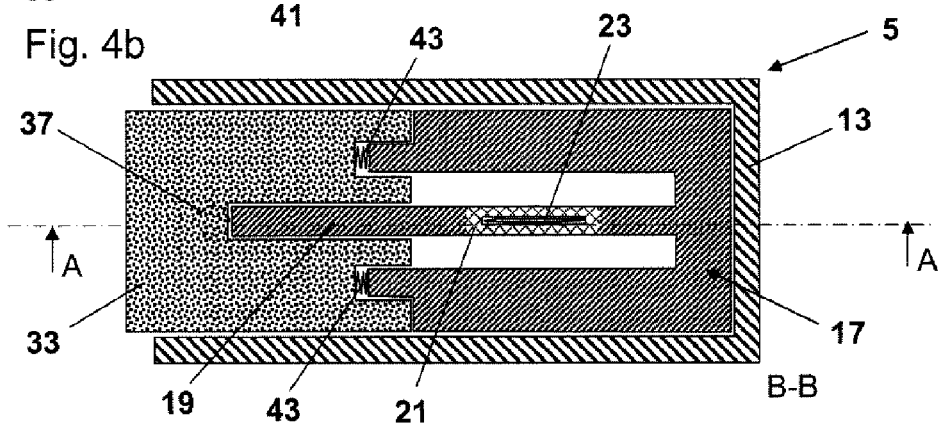

VALVE SYSTEM FOR A FLUID CHANNEL

BACKGROUND OF THE INVENTION

The present invention relates to a valve system connectable to a fluid channel, wherein the valve system comprises an actuating means and a closing element for selectively closing and opening of the channel.

Fluid channels in the form of discharging extensions may be connected to fluid containers such as tubes, bottles, barrels, tanks or bags. In many cases the fluid container and/or the fluid channel are connected to a closing mechanism such as a sealing lid to prevent evaporation, leakage or a contamination caused by a contact between the fluid and the outer atmosphere during storage. However, during discharging of the fluid most of the known fluid containers do not prevent a contact between the fluid in the container and air or they even support the intrusion of air.

However, in specific applications it is very important that the fluid contained in the container does not get in contact with the outer atmosphere at all. This may for example be the case for certain medical products, sterile solutions, pharmaceutical products, fungicides, antibacterials, disinfectants, preservative agents, hygiene products, sanitary products or industrial processing products such as drugged oil, lubricants or cooling agents. For many of such fluid products a small contamination with air may have already a negative influence on the fluid quality and the applicability of the fluid for its intended use. Especially for manually manageable fluid containers which may be spatially oriented in any direction, i.e. in an upright storage position, an upside-down discharging position or any position in between, a special valve system is required to provide the possibility to discharge the fluid without letting air into the container.

In order to prevent an inflow of air through the opening of a compressible fluid container such as a collapsible tube before, during and after discharging of fluid, EP 1 772 392 A2 describes a valve system having a closing member with a resilient portion such that the closing member is capable of being deformed in a direction of an outward fluid flow caused by an excess pressure in the container. As soon as the outward fluid flow stops the resilient portion of the closing member closes the opening such that no air may enter the container. The elastic resilience of the tube material causes an under pressure in the container such that the closing member is further pressed into a sealing position to close the opening.

This design has several disadvantages. Firstly, for discharging fluid it is necessary to manually compress the collapsible tube container in order to produce the required excess pressure in the container. An automatic outflow of the fluid under its gravitational force alone is not possible. Secondly, due to the elastic stiffness of the resilient tube material there is a constant under pressure present during storage of the fluid in the container. A tiny or creeping leakage will therefore result in an inward flow of air contaminating the fluid. Thirdly, the valve system may open in any spatial orientation of the container. This is a potential risk for accidental opening in an undesirable position. A desired spatial orientation of the container for discharging the fluid may for instance be an upside down orientation in which the opening is located below the fluid level. A discharging in any other orientation may be undesirable. The valve system described in the EP 1 772 392 A2 works independently of the spatial orientation of the container and therefore poses a risk of accidental opening in an undesirable orientation.

SUMMARY OF THE INVENTION

Accordingly, it is the object of the present invention to provide a valve system connectable to a fluid channel of a fluid container, wherein the valve system is capable of preventing an inflow of air into the container before, during and after discharging of fluid. Furthermore, the valve system should, inter alia for safety reasons, not be openable when the valve system is positioned in certain spatial orientations, for example orientations in which the opening is located above the fluid level.

According to a first aspect of the present invention a valve system connectable to a fluid channel is provided, wherein the valve system comprises an actuating means and a closing element for selectively closing and opening of the channel, wherein the valve system comprises a chamber which contains a movable coupling member, which can adopt at least two positions, wherein a section of the coupling member is located within the chamber in at least one position of the coupling member and the coupling member is capable of moving under its gravitational force into a transfer position in which the coupling member may transfer to the closing element an external force acting on the actuating means towards the closing element.

The section of the coupling member may, in this case, be formed integrally with the movable coupling member or be a movable component connected to the coupling member. The actuating means may for example be a button which may be pressed manually. If the coupling member is located in the transfer position, which can be the case e.g. when at least half of the cross-section of the coupling member is arranged in a gap between the actuating means and the closing element, a manual shift of the actuating means is transferred to the closing element which opens the channel. As the coupling member is movable and able to find its way into the transfer position under its gravitational force only, it is only possible to open the channel in a defined spatial orientation of the valve mechanism.

For example, the fluid channel may be a discharging channel connected to a fluid container and the valve system may be connected to the channel such that it is only possible to open the channel in a spatial orientation of the container in which the channel is located below the fluid level in order to allow an outflow of the fluid. In this position the coupling member will move into the transfer position under its gravitational force. However, other orientations of the valve system will result in the coupling member leaving the transfer position such that a movement of the actuating means is not transferred to the closing element which then keeps closing the channel.

The coupling member may be located almost completely inside the chamber and the gravitational force may be generated by the force of the weight of the movable coupling member itself. For example, the coupling member may be a ball member of spherical shape, wherein the ball member is freely movable inside the chamber. A ball as a coupling member has the advantage that it is able to roll and/or fall into the transfer position independent of its spatial orientation.

However, it will be appreciated that the coupling member may have any shape if the chamber is designed in such a way that the coupling member is capable of moving under its gravitational force into the transfer position.

It is also possible that only a section of the movable coupling member protrudes into the chamber and the gravitational force is generated by the force of the weight of a movable body additionally located in the chamber. For example, the movable coupling member may be pivotably connected to the actuating means and be capable of pivoting into a transfer position by the force of the weight of a movable body located in the chamber.

Preferably, the valve system comprises a movably arranged support element which is capable of moving under its gravitational force into a support position to support the coupling member from below.

The support element has the effect that even a small deflection out of the spatial opening orientation in which the valve system may open results in the coupling member leaving the transfer position. Without the movable support element the coupling member would be relatively stable in the transfer position, and only large deflections of the spatial orientation, e.g. turning upside-down, would result in the coupling member leaving the transfer position. The support element may, however, be arranged to block the transfer position for smaller deflections already. If, for example, the transfer position is the deepest position in a gap between the actuating means and the closing element the support element may support the coupling member from below. The contact surface between the support element and the coupling member may rise upon a certain deflection of the spatial orientation such that the gap between the actuating means and the closing element is not deep enough to receive the entire lower half of the coupling member. Thereby, the coupling member can not reach the transfer position which is blocked by the support element.

The support element is preferably arranged to allow the coupling member to move into the transfer position only when the support element is in the support position. The support position may be the position of the support element in which the support surface between the coupling member and the support member has the least altitude.

It may be appreciated that it is advantageous if the gravitational force on the support element is larger than the gravitational force on the coupling member such that the support element is able to push the coupling member out of the transfer position. The support element may therefore be larger and made of the same material as the coupling member or it may be of the same size or smaller and made of a material with a larger specific gravity.

According to a first preferred embodiment of the invention the support element is a spherical body being movably arranged on a receiving surface shaped in the form of a spherical or conical recess, and the coupling member preferably has a circular cross-section. The receiving surface can be shaped in any rotational-symmetric way providing a differentiable or non-differentiable radially outward rising gradient. Due to the influence of its gravitational force the spherical body may leave the central support position when the valve system is deflected from its initial spatial orientation.

If, for example, the receiving surface is shaped as a conical recess with a cone angle of 150 degrees the spherical body will leave the support position for a radially more outward position when the valve system is tilted by more than 15 degrees out of the position for which an opening of the valve system should be allowed, i.e. when the channel is located below the fluid level. When the spherical body follows the radially outward rising slope it rises with respect to the gap between the actuating means and the closing element. Due to this rise the contact surface between the spherical body and the coupling member rises as well such that the coupling member can not reach the transfer position or it is pushed out of it. Less than a half of the coupling member is then located in the gap between the actuating means and the closing element. If the actuating means is then manually pressed towards the closing element the coupling member is squeezed out of the gap such that the actuating means only fills the gap without a transfer of the force towards the closing element which stays in the closing position.

Only when the spherical body is in the central support position, e.g. when the channel is located vertically below the fluid within 15 degrees of tilting angle, the coupling member is able to reach the transfer position in which half of the coupling member or more is located in the gap between the actuating means and the closing element. If the actuating means is then manually pressed towards the closing element the coupling member in the gap transfers the force towards the closing element which then opens.

It will be appreciated that a receiving surface shaped in the form of a spherical recess should have a curvature radius smaller than the sum of the diameter of the (in this case preferably) spherical body and the radius of the coupling member.

According to a second preferred embodiment of the invention, it is possible to dispense with a supporting element in the valve system. In this case, only a section of the movable coupling member protrudes into the chamber and the gravitational force is generated by the force of the weight of a movable body additionally located in the chamber. For example, the movable coupling member may be pivotably connected to the actuating means and be capable of pivoting into a transfer position by the force of the weight of the movable body located in the chamber.

According to a third preferred embodiment of the invention the support element is a pendulum wherein the pivot point of the pendulum, the centre of mass of the pendulum and the centre of mass of the coupling member, which in this case preferably has a circular cross-section, are positioned on one vertical axis when the coupling member is in the transfer position. It is preferred that in this situation the coupling member is located vertically above the pivot point wherein the latter is located above the centre of mass of the pendulum. However, it will be appreciated that the centre of mass of the pendulum and/or the pivot point of the pendulum may also be located vertically above the coupling member when the coupling member is in the transfer position.

The pendulum may comprise a ball joint portion with a partially spherical surface arranged in a ball joint socket portion of the valve system, a first arm extending into one direction from the ball joint portion towards a receiving portion of the support element and a second arm extending into the opposite direction from the ball joint portion towards a weight portion of the support element wherein the receiving portion is adapted to support the coupling member from below.

This embodiment has the advantage that a leverage effect of the pendulum may support the vertical alignment of the support element. Due to the gravitational force of the weight portion the first arm and the second arm will be aligned along the vertical axis for a large range of tilting positions of the valve system as long as the limit of the mobility of the pendulum is not reached. Therefore, it may be advantageous if the second arm is longer than the first arm. The receiving portion may comprise a contact surface shaped in the form of a spherical recess with a curvature radius corresponding to the radius of the coupling member. In the central support position of the pendulum the contact surface is located directly below the transfer position such that the coupling member in the transfer position rests on the contact surface. When the valve system is tilted relative to the vertical axis the pendulum does not follow the deflection such that the gap moves relative to the contact surface of the pendulum. A part of the receiving portion of the pendulum then blocks the space needed by the coupling member to take the transfer position such that the coupling member is either pushed out of the transfer position or it cannot reach it any more as long as the valve system is in a tilted position. It is to be understood that there is a certain range of tilting angles relative to the vertical axis for which the transfer position is not blocked, e.g. for tilting angles below 15 degrees relative to the vertical axis. Only in this range opening of the valve system is possible.

Preferably, the channel is flexible and the closing element is capable of clamping the channel by a resilient force and the channel can be unclamped by an external force transferred towards the closing element via the coupling member. The resilient force may be an inner restoring force of an elastic portion of the closing element which tends towards an initial shape corresponding to the closing state of the closing element. The external force may be a manual pressing force transferred from the actuating means via the coupling member to the closing element. Under the influence of the external force an elastic portion of the closing element may be deformed against its inner restoring force into a shape corresponding to the opening state of the closing element. The closing element may therefore be preloaded into a closing state.

In a preferred embodiment of the valve system the closing element comprises an elastic portion with an inner slit opening such that the channel is able to pass through the slit opening of the elastic portion of the closing element. The opening in the shape of the slit having parallel side edges is the initial shape corresponding to the closing state of the closing element. In this shape the passage opening of the flexible channel which is fed through the slit is reduced to zero such that the flexible channel is closed. If an external force is applied to the closing element, the initial slit opening may deform to have a shape with an oval cross-section such that the flexible channel may radially expand into a corresponding passage opening such that the flexible channel is then open and fluid may pass through the channel.

Preferably, the inner slit opening of the elastic portion of the closing element unclamps the channel by expanding upon a force acting on the closing element towards the channel and in a transverse direction with respect to the channel passing through the slit opening. The resilient force of the elastic portion may be a pressing force essentially from two sides in a transverse direction with respect to the channel. The external force exerted by the actuating means may also act from two sides in a transverse direction with respect to the channel but essentially perpendicular to the resilient force. The closing element may be fixed to the valve system at one side such that the reaction force opposing the external force during the deforming of the elastic portion is provided by the system itself.

In a preferred embodiment of the valve system the actuating means are spring-loaded away from the channel in a transverse direction with respect to the channel providing a gap between the actuating means and the closing element adapted to receive the coupling member. Thereby, it is ensured that the gap is opened as long as the actuating means are not actuated such that the coupling member can fall or roll into the gap. Moreover, the actuating means, e.g. a button, takes automatically a position in which it is ready to be actuated.

According to a second aspect of the present invention a fluid container is provided comprising a channel for discharging fluid from the container, the channel being connected to a described inventive valve system, wherein the fluid container comprises flexible material such that the inner volume is able to essentially conform with the volume of the fluid intended to be contained in the container.

The inventive fluid container ensures that there is no under pressure built up inside the container by discharging fluid.

The discharged volume is not refilled by air or another gas as the flexible material conforms with the volume currently contained in the container, i.e. reduces in volume during discharging of fluid. Thereby, the fluid can flow out automatically without the need to build up an overpressure by manual force or other means. This is especially important in combination with the inventive valve system which is adapted to prevent any inflow of air into the container.

Preferably, the coupling member is in the transfer position only when the fluid container has a spatial orientation such that the channel and the valve system connected thereto are positioned below the level of the fluid intended to be contained in the fluid container, more particularly with the fluid container having a longitudinal axis with an inclination of 15 degrees or less with respect to the vertical axis.

In order to facilitate the handling of the flexible fluid container which may be a collapsible bag comprising a flexible polymer material it is advantageous if it is framed by a rigid casing. The valve system may be connected to the casing by means of a threaded connection or the like. The casing is not air-tight such that the contained flexible fluid container may freely collapse during discharging of fluid without building up an under pressure inside the casing.

BRIEF DESCRIPTION OF THE DRAWINGS

In the following, preferred embodiments are discussed in further detail with reference to the accompanying FIGS. 1 to 14.

FIGS. 1a and 1b show a first preferred embodiment of a closed inventive valve system connected to a flexible channel of a fluid container in an upside down discharge position.

FIGS. 4a and 4b show the first preferred embodiment of an actuated and closed inventive valve system connected to a flexible channel of a fluid container having a tilted spatial orientation relative to the vertical axis.

DESCRIPTION OF PREFERRED EMBODIMENTS

Figure 2A:
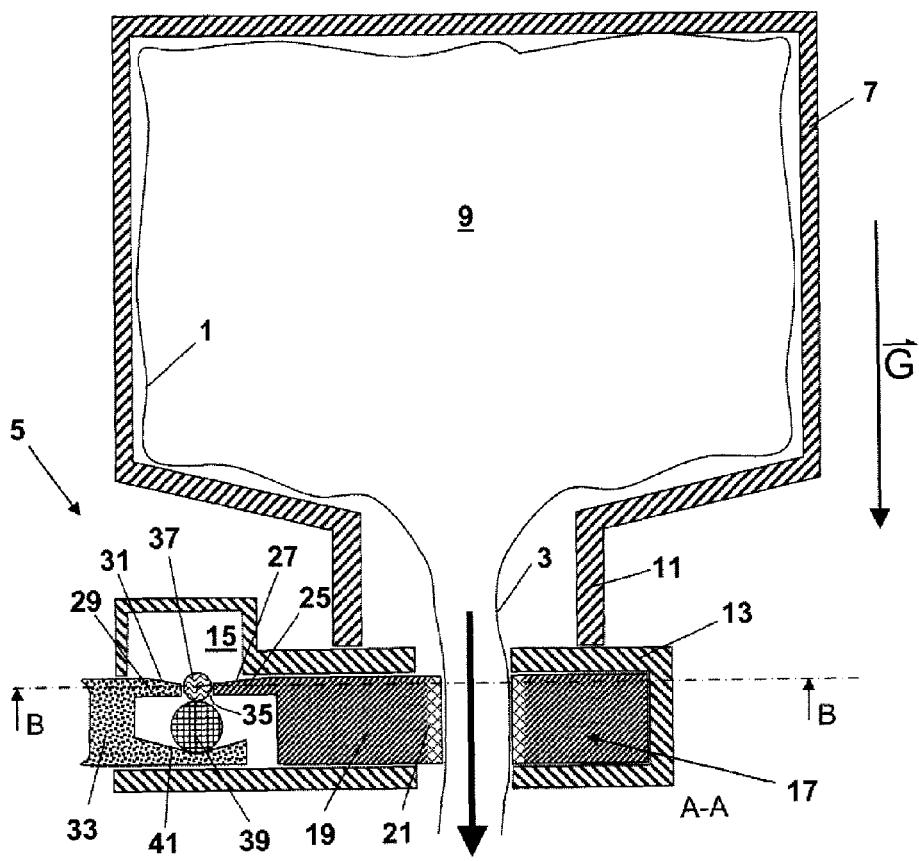
FIGS. 2a and 2b show the first preferred embodiment of an opened inventive valve system connected to a flexible channel of a fluid container in an upside down discharge position.

In FIGS. 1a and 1b a fluid container 1 with a flexible channel 3 for discharging the container 1, the channel 3 being connected to a valve system 5, are shown in an upside down discharge position. The fluid container 1 in the form of a flexible bag is framed by a rigid casing 7 which is adapted to contain the volume of the fluid container 1 filled with a fluid 9. The rigid casing 7 has a bottle-like shape with a main volume and a bottle-neck 11 containing the channel 3. The valve system 5 comprises a frame 13 essentially framing the relevant parts of the valve system 5. The frame 13 is fixed to the bottle-neck 11 of the rigid casing 7 of the fluid container 1. There is no air-tight sealing between the casing 7 and the valve system 5 such that air can enter the main volume of the casing 7. This is important in order to ensure that the flexible fluid container 1 can collapse freely without causing an under pressure during discharging of the fluid 9. The frame 13 comprises a through-going passage through which the channel 3 is fed.

Furthermore, the valve system 5 comprises an inner closed chamber 15 with outer walls formed by the frame 13 of the valve system 5. Inside the frame 13 of the valve system 5 a closing element 17 is located which comprises an elongate web 19 extending into a transverse direction with respect to the channel 3. The elongate web 19 of the closing element 17 comprises a resiliently elastic portion 21 with an inner slit opening 23 at the through-going passage of the frame 13. The flexible channel 3 is squeezed to a flat shape and fed through the slit opening 23 of the resiliently elastic portion 21 by the closing element 17. In this flat shape the channel 3 has no inner passage such that it tightly seals the container 1 and the fluid 9 cannot discharge.

One end of the elongate web 19 of the closing element 17 is fixed to the frame 13 of the valve system 5. The other end is free and comprises a first contact portion 25 having a first bevelled surface 27 forming a portion of a wall of the chamber 15. The elastic portion 21 of the elongate web 19 is located between the fixed end and the free end.

Another portion of a wall of the chamber 15 is formed by a second contact portion 29 having a second bevelled surface 31 which is part of an actuating means 33. The actuating means 33 is essentially a slidably mounted button which can be pressed by a user towards the channel 3 in the longitudinal direction of the elongate web 19. The first contact portion 25 of the elongate web 19 and the second contact portion 29 of the actuating means 33 have a distance to each other forming a gap 35 in which a coupling member 37 in the form of a spherical ball member is located. The maximum width of the gap 35 corresponds essentially to the diameter of the coupling member 37.

The coupling member 37 is supported from below by a support element in the form of a spherical body 39 which is larger and heavier than the coupling member 37. The spherical body 39 is movably arranged on a receiving surface 41 shaped in the form of a conical recess. The receiving surface 41 is part of the actuating means 33 and has its central point vertically below the centre of the gap 35 in which the coupling member 37 resides on the spherical body 39. The receiving surface 41 is shaped in the form of a conical recess with a cone angle of 150 degrees. This means that the spherical body 39 resides in a recess with a radially outward rising slope of 15 degrees.

The bevelled surfaces 27, 31 of the first contact portion 25 of the elongate web 19 and the second contact portion 29 of the actuating means 33, respectively, form as part of a wall of the chamber 15 a radially inward falling slope towards the gap 35 to guide the coupling member 37 into the gap 35. As long as the spherical body 39 resides at the central point of the receiving surface 41, i.e. the support position, the coupling member 37 may fall into the gap 35 with at least half of its diameter, i.e. into the transfer position. In the transfer position the coupling member 37 is able to transfer a manual pressing force which a user exerts on the actuating means 33 from the second contact portion 29 to the first contact portion 25 of the free end of the elongate web 19 and thus to the closing element 17.

Figure 2B:
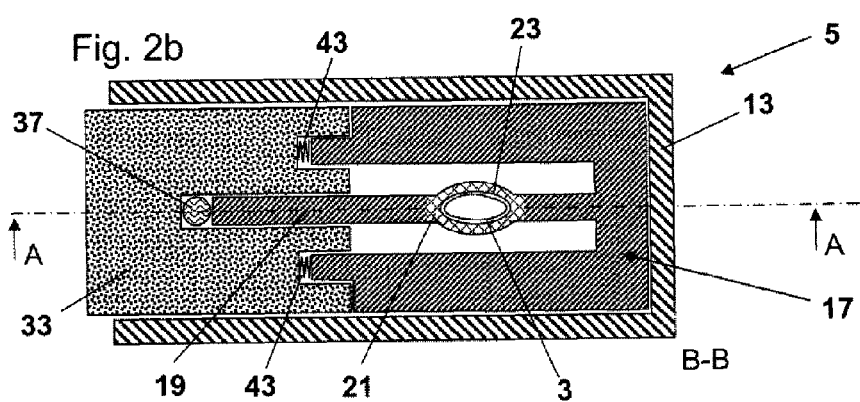

In the shown upside down orientation of the container 1 in which the channel 3 is located below the level of the fluid 9 contained in the volume of the fluid container 1 the elongate web 19 may be upset by a pressing force applied to the actuating means 33. This is shown in FIGS. 2a and 2b. The actuating means 33 is pressed towards the channel 3 such that the free end of the elongate web 19 is pushed towards the channel 3. As the other end of the elongate web 19 is fixed to the frame 13, the resiliently elastic portion 21 through which the channel 3 passes is upset such that it bulges. The inner slit opening 23 widens to an oval opening. The hydrostatic pressure of the fluid 9 residing in the volume above the channel 3 widens the channel 3 as the resilient elastic portion 21 does not clamp the channel 3 to a flat shape anymore. The valve system 5 is opened and the fluid 9 can discharge automatically under its gravitational force.

It can be seen from FIGS. 1b and 2b that the actuating means 33 are spring-loaded away from the channel 3 by springs 43. The manual pressing force on the actuating means 33 must therefore overcome the repulsive force of the springs 43 and the resilient force of the elastic portion 21. The springs 43 ensure that the gap 35 between the actuating means 33 and the closing element 17 is large enough to receive the coupling member 37 when the actuating means 33 is not in an actuated state.

Figure 3A:
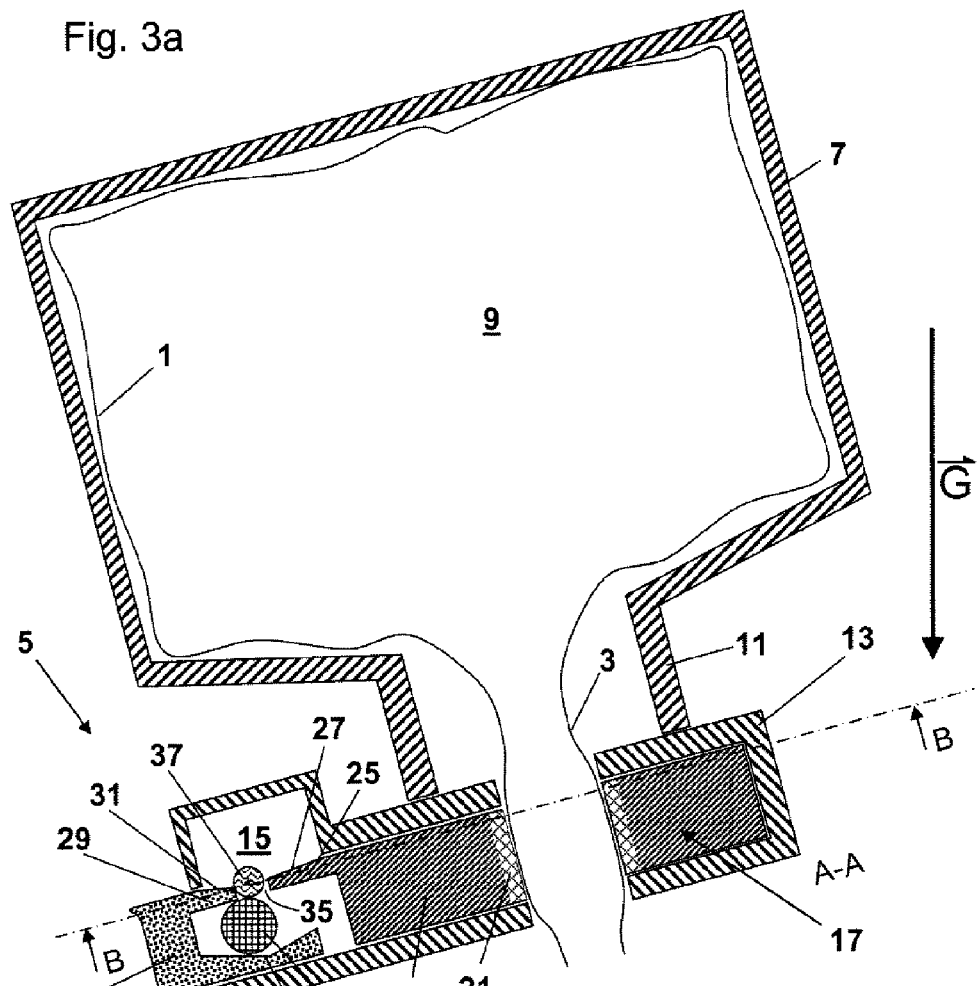
FIGS. 3a and 3b show the first preferred embodiment of an inventive valve system connected to a flexible channel of a fluid container having a tilted spatial orientation relative to the vertical axis.
Figure 3B:
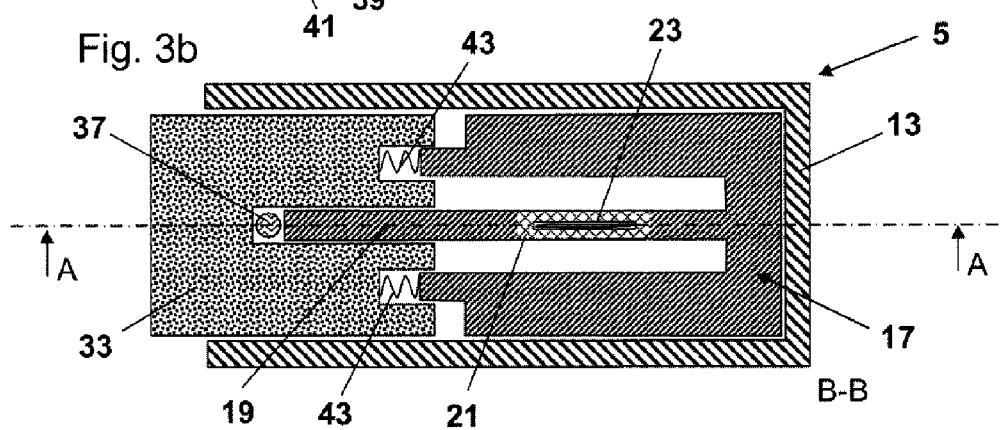

FIGS. 3a and 4a show the fluid container 1 in a tilted spatial orientation relative to the vertical axis which is illustrated by the arrow indicating the direction of the gravitational force G. The tilting angle is slightly more than 15 degrees such that the centre point of the receiving surface 41 is not the point of least altitude on the receiving surface 41. The gravitational force of the spherical body 39 urges the spherical body 39 to roll out of the central support position to a shifted position shown in FIG. 3a. This shift results in a rise of the contact surface between the spherical body 39 and the coupling member 37 with respect to the gap 35. Therefore, the coupling member 37 is pushed up by the heavier spherical body 39 in case the coupling member 37 resides in the gap 35. Only less than half of the diameter of the coupling member 37 is able to protrude into the gap 35 in this situation. In case the coupling member 37 is somewhere else in the chamber 15 the shifted position of the spherical body 39 leads to the fact that the transition position, i.e. the position in which at least half of the diameter of the coupling member 37 is located in the gap 35, is blocked by the spherical body 39.

FIGS. 4a and 4b show what happens if the actuating means 33 are actuated in this tilted position of the valve system 5. A manually applied pressing force on the actuating means 33 is not transferred from the second contact portion 29 of the actuating means 33 to the first contact portion 25 of the free end of the elongate web 19. Instead, the coupling member 37 is squeezed out of the gap 35, because less than half of it resides in the gap 35. Therefore, the pressing force only moves the actuating means 33 to compress the springs 43 and to reduce the gap 35 between the actuating means 33 and the closing element 17. The elongate web 19 is not upset and the valve system 5 does not open. The valve system 5 is thereby prevented from opening in a tilted spatial orientation relative to the vertical axis. It will be appreciated that the range of tilting angles for which an opening is allowed is determined by the slope or the curvature of the receiving surface 41 on which the spherical body 39 is located.

Figure 5A:
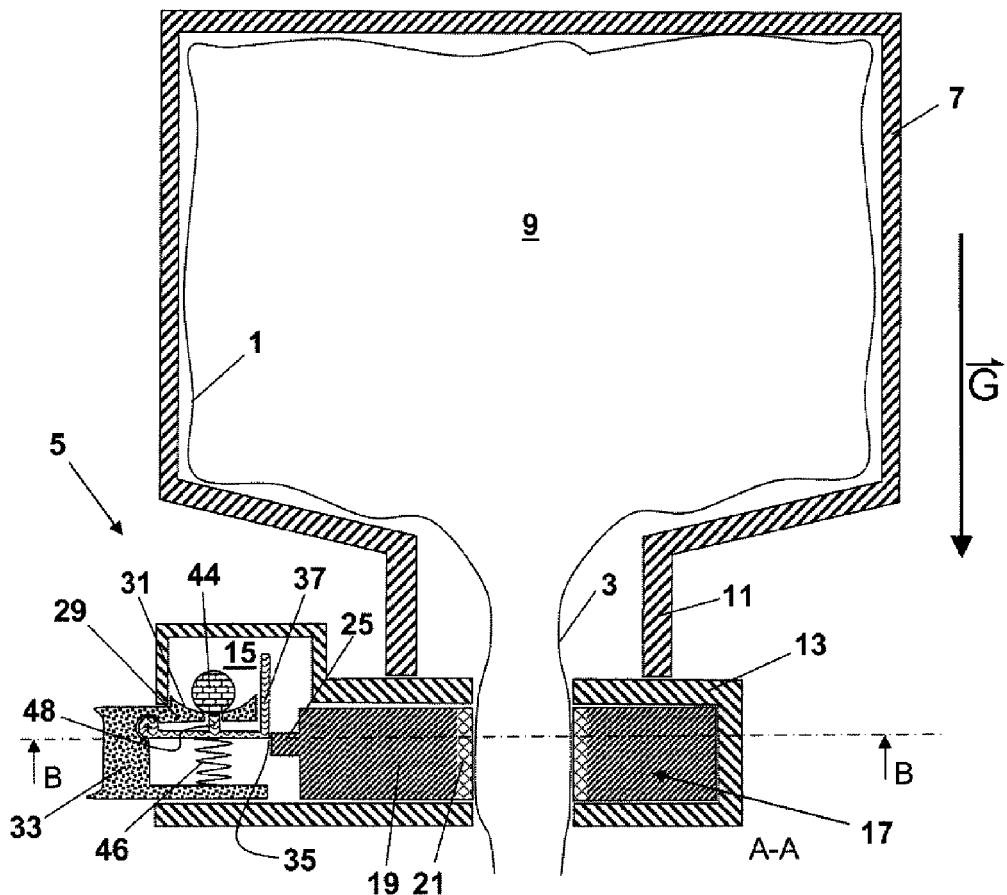
FIGS. 5a and 5b show a second preferred embodiment of an inventive valve system connected to a flexible channel of a fluid container in an upside down discharge position.
Figure 5B:
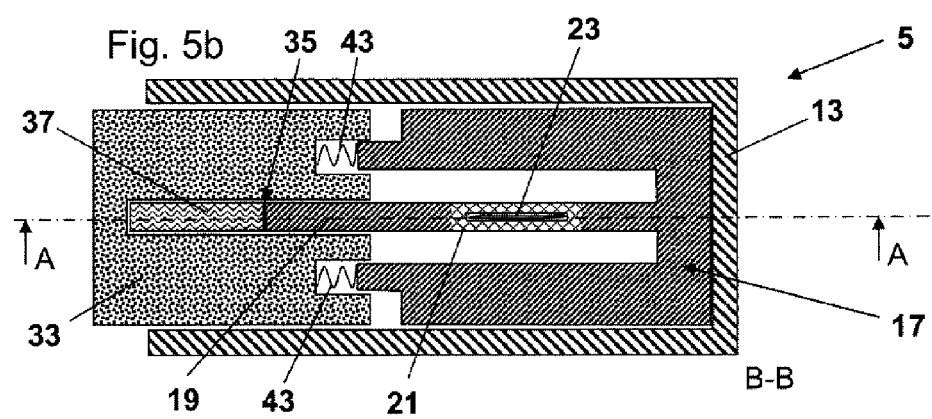

A second embodiment of the present invention is shown in FIGS. 5a,b to 8a,b. In the case of this embodiment, the coupling member 37 is designed in the form of a pivotably articulated lever arm. The coupling member 37 is connected to the actuating means 33 such that it is mounted pivotably about an axis, wherein the axis runs in the horizontal direction when the fluid container 1 is in the vertical position represented. On the underside, the coupling member 37 is pressed upwards, supported by a supporting spring 46. Above the coupling member 37 there extends the second contact portion 29, designed essentially as the bottom of the chamber 15, with the second surface 31. In this embodiment, the second surface 31 of the second contact portion 29 forms a spherical or conical recess with a central hole, through which the coupling member 37 protrudes partially into the chamber 15 from below with a section 48 in the form of a projection. The further limitations of the chamber 15 are formed by the frame 13 and part of the coupling member 37.

As shown in FIG. 5a, located within the chamber 15 is a freely movable spherical body 44, which in a central position lies on the recess formed by the second surface 31. In this position, the body 44 presses the section 48 of the coupling member 37 that is protruding into the chamber 15 downwards, so that the coupling member 37 is pivoted into the transfer position by the force of the weight of the body 44. For this purpose, the weight of the body 44 must be great enough to overcome the resilient force of the supporting spring 46 and press the coupling member 37 downwards.

Figure 6A:
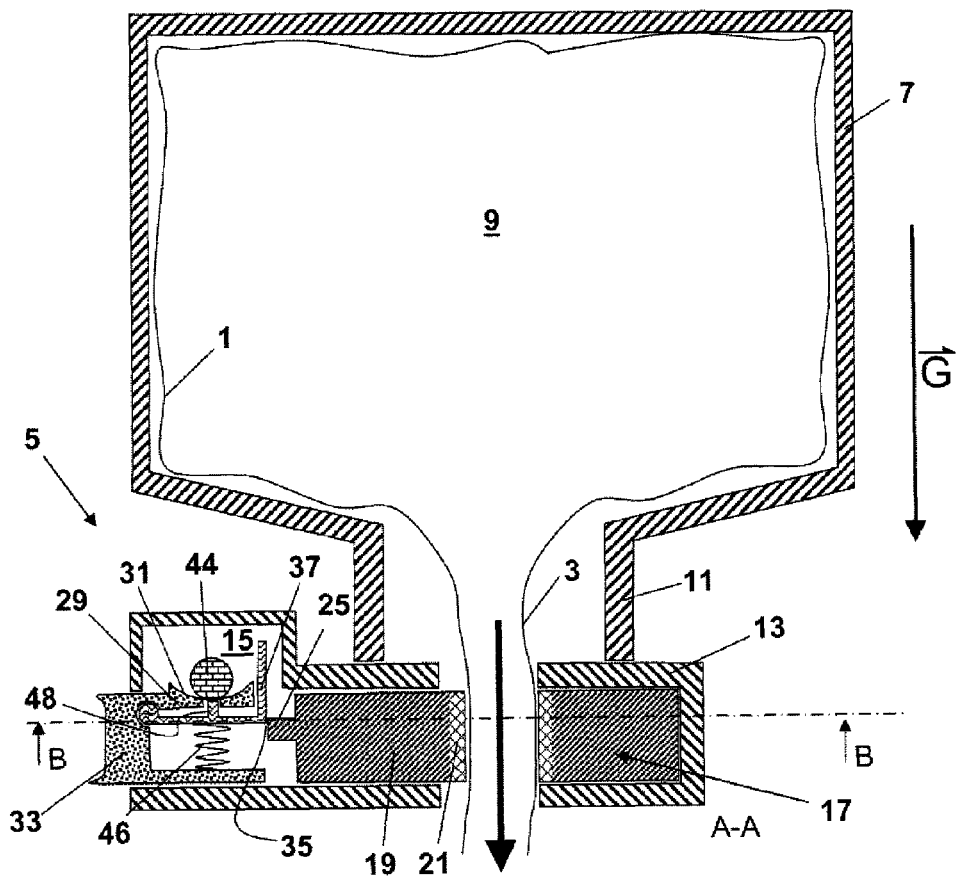
FIGS. 6a and 6b show the second preferred embodiment of an opened inventive valve system connected to a flexible channel of a fluid container in an upside down discharge position.
Figure 6B:
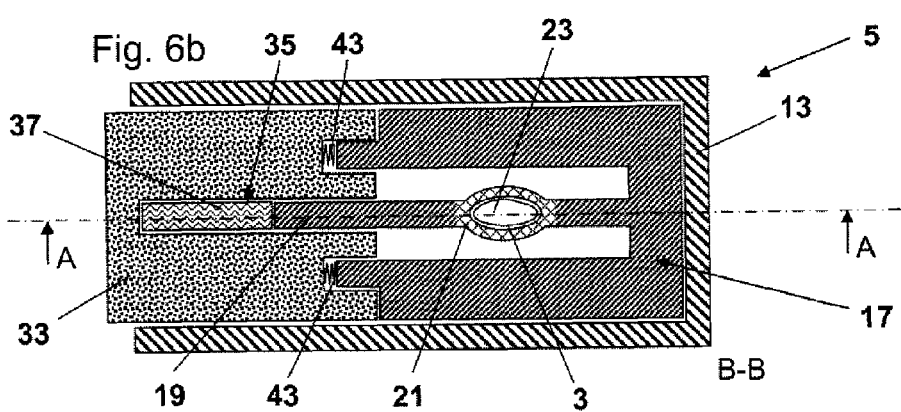

It is shown in FIGS. 6a, b how the coupling member 37 in the transfer position brings about a force closure between the actuating means 33 and the elongate web 19 on account of the gravitational force of the body 44, i.e. transfers an external force which acts on the actuating means 33 in the direction of the closing element 17. The actuating means 33 are moved towards the channel 3 such that the free end of the elongate web 19 is moved towards the channel 3. As the other end of the elongate web 19 is fixed to the frame 13, the resiliently elastic portion 21 through which the channel 3 passes is upset such that it bulges. The inner slit opening 23 widens to an oval opening. The hydrostatic pressure of the fluid 9 residing in the volume above the channel 3 widens the channel 3 as the resilient elastic portion 21 does not clamp the channel 3 to a flat shape any more. The valve system 5 is opened and the fluid 9 can discharge automatically under its gravitational force.

Figure 7A:
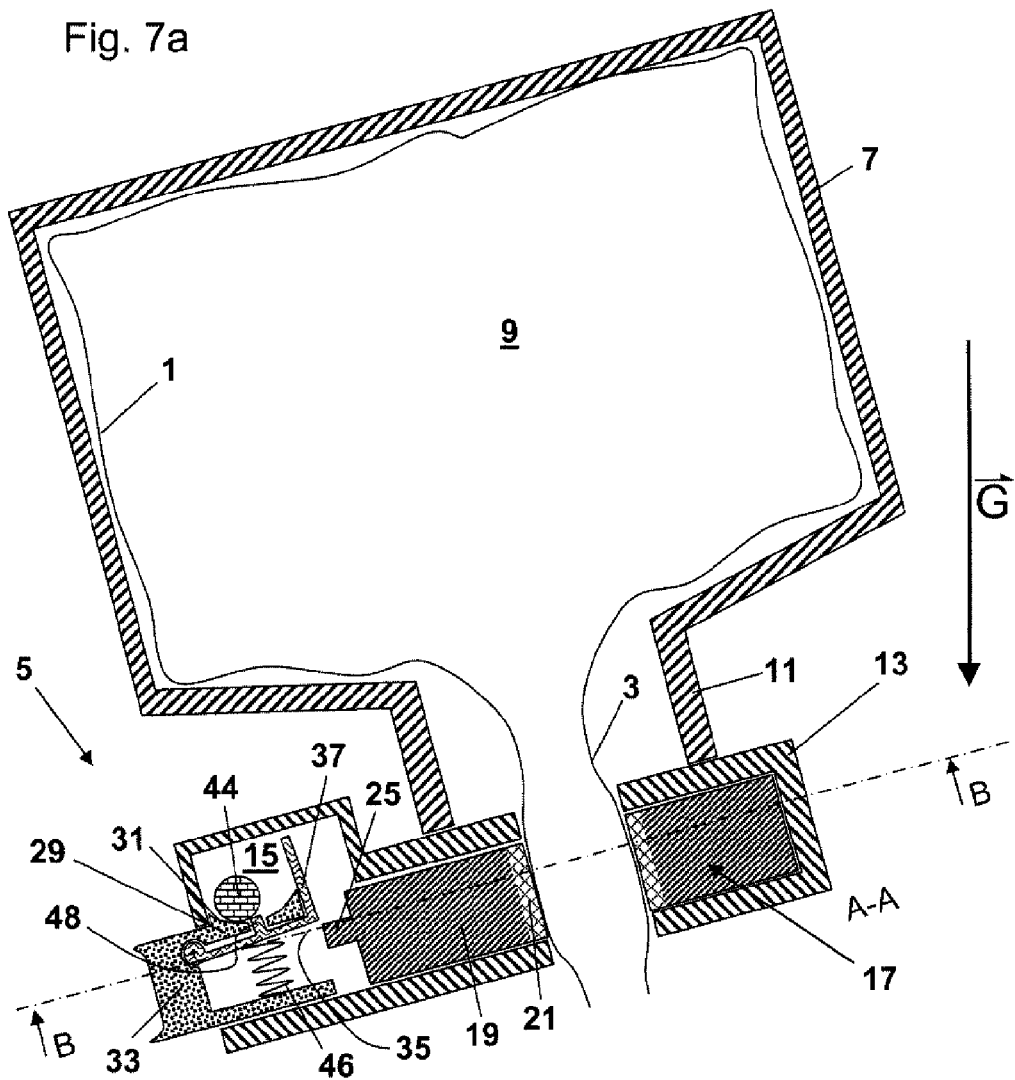
FIGS. 7a and 7b show the second preferred embodiment of an inventive valve system connected to a flexible channel of a fluid container having a tilted spatial orientation relative to the vertical axis.
Figure 7B:
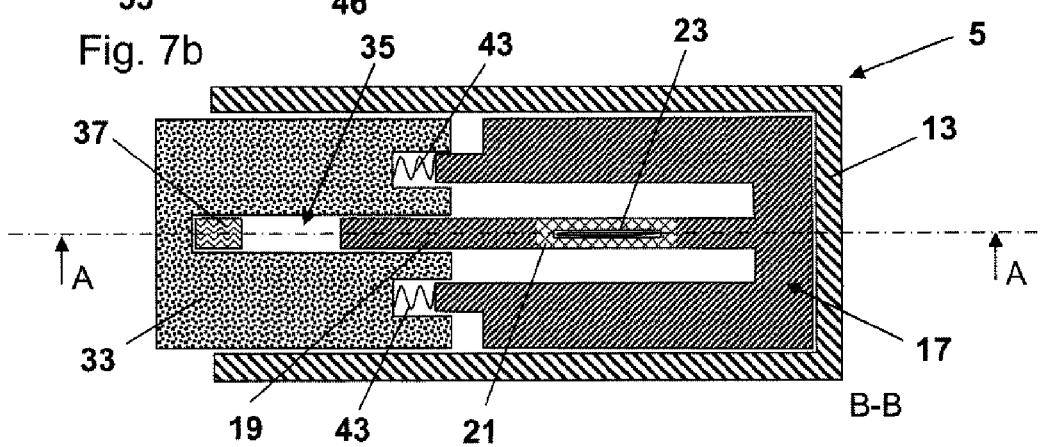
Figure 8A:
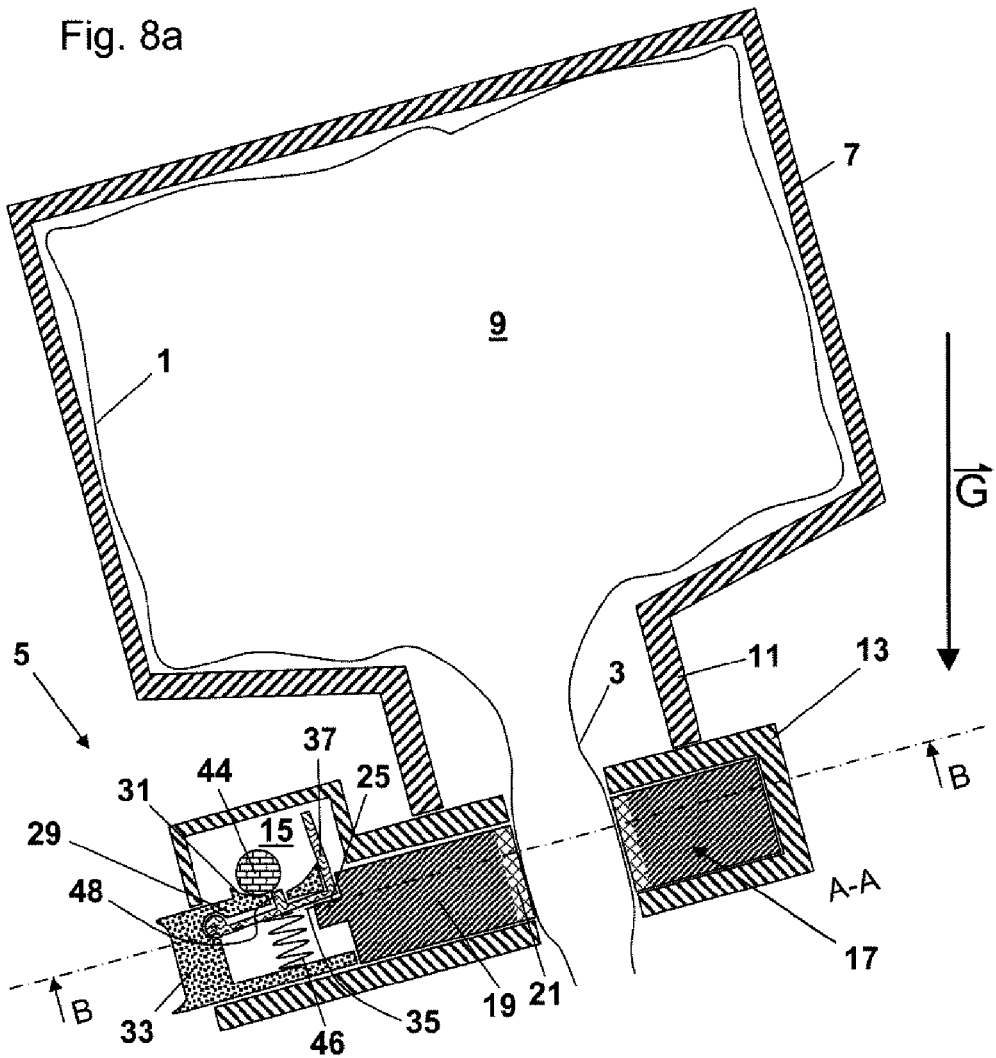
FIGS. 8a and 8b show the second preferred embodiment of an actuated and closed inventive valve system connected to a flexible channel of a fluid container having a tilted spatial orientation relative to the vertical axis.

By analogy with FIGS. 3a and 4a, the fluid container 1 is shown in FIGS. 7a and 8a in a tilted spatial orientation relative to the vertical axis. The force of the weight of the movable body 44 located in the chamber 15 has the effect that the body 44 rolls out of the central position in the recess of the surface 31 to a shifted position, which is shown in FIG. 7a. This shift has the effect that there is no longer any pressure exerted downwards on the section 48 of the coupling member 37 that protrudes into the chamber 15 and the supporting spring 46 on the underside presses the coupling member 37 upwards out of the transfer position. This creates a gap 35 between the coupling member 37 and the first contact portion 25 of the elongate web 19, since there is no longer a force closure between them as soon as the coupling member has left the transfer position.

Figure 8B:
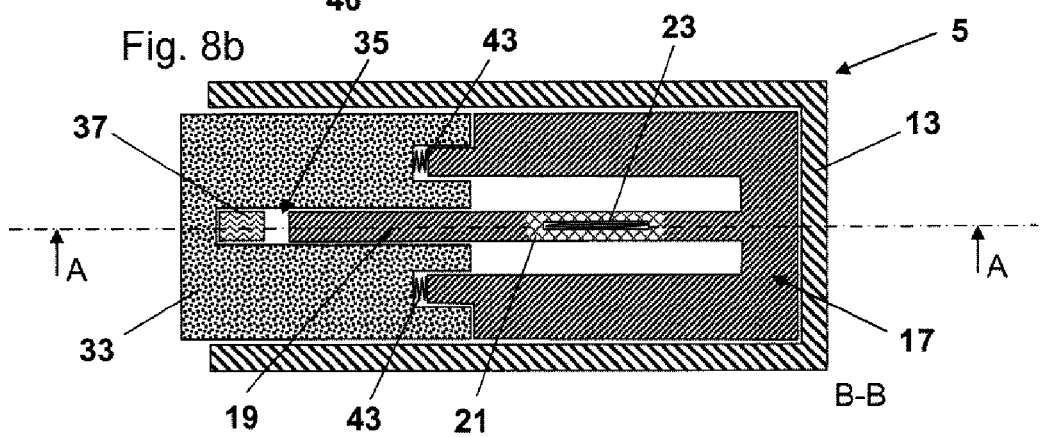

FIGS. 8a and 8b show what happens if the actuating means 33 are actuated in this tilted position of the valve system 5. A manually applied pressing force on the actuating means 33 is not transferred from the actuating means 33 to the first contact portion 25 of the free end of the elongate web 19. Instead, the coupling member 37 is pushed past the first contact portion 25 of the free end of the elongate web 19, since the coupling member 37 has left the transfer position. Therefore, the pressing force only moves the actuating means 33 to compress the springs 43. The elongate web 19 is not upset, and the valve system 5 does not open. The valve system 5 is thereby prevented from opening in a tilted spatial orientation relative to the vertical axis. It will be appreciated that the range of tilting angles for which an opening is allowed is determined by the slope or the curvature of the second surface 31 and the size of the movable body 44.

Figure 9:
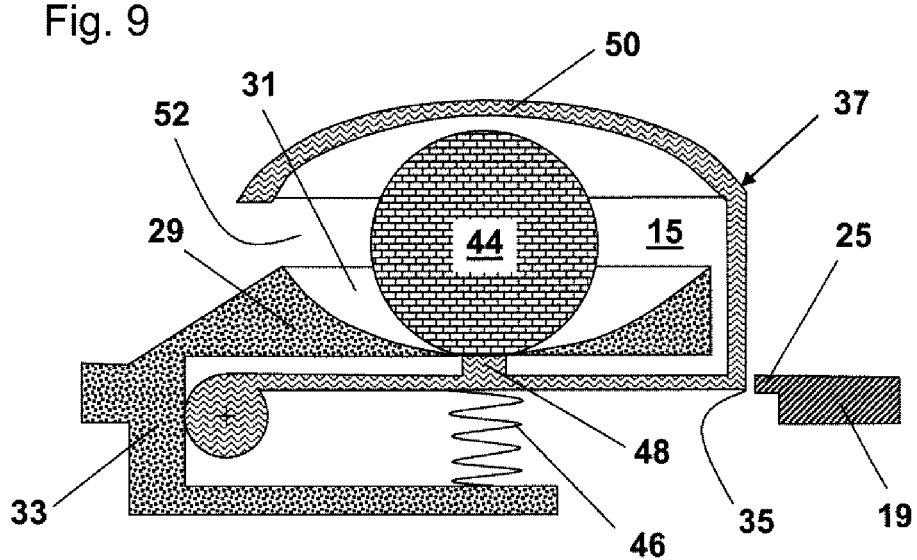
FIGS. 9 and 10 show views of details of an alternative design of the second preferred embodiment of an inventive valve system in an upside down orientation and a tilted spatial orientation relative to the vertical axis.
Figure 10:
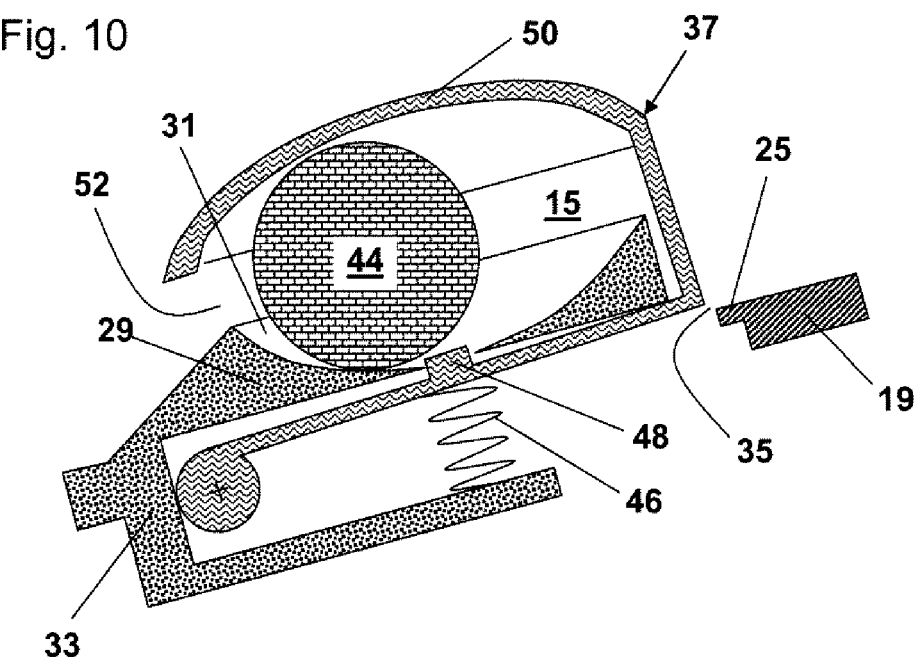

Part of the coupling member 37 may, as shown in FIGS. 9 and 10, also extend in the form of a shell 50 on the upper side over the second surface 31 of the second contact portion 29 and consequently form the chamber 15, so that the frame 13 does not have to form walls of the chamber 15. It will be appreciated here that the chamber 15 does not have to be tightly sealed off, but merely has to be designed to limit the freedom of movement of the movable body 44 located in it. The chamber 15 may therefore also have openings which are small enough that the body 44 cannot leave as a result. The same applies correspondingly to the chamber 15 in the first and third exemplary embodiments with respect to the coupling member 37 located entirely in it. In FIGS. 9 and 10, the recess of the second surface 31 of the second contact portion 39 and the shell 50 on the upper side of the coupling member 37 form the chamber 15, which has between the recess and the shell 50 on the upper side a horizontal slit 52, which is however narrow enough that the movable body 44 located in the chamber 15 cannot leave.

Figure 11A:
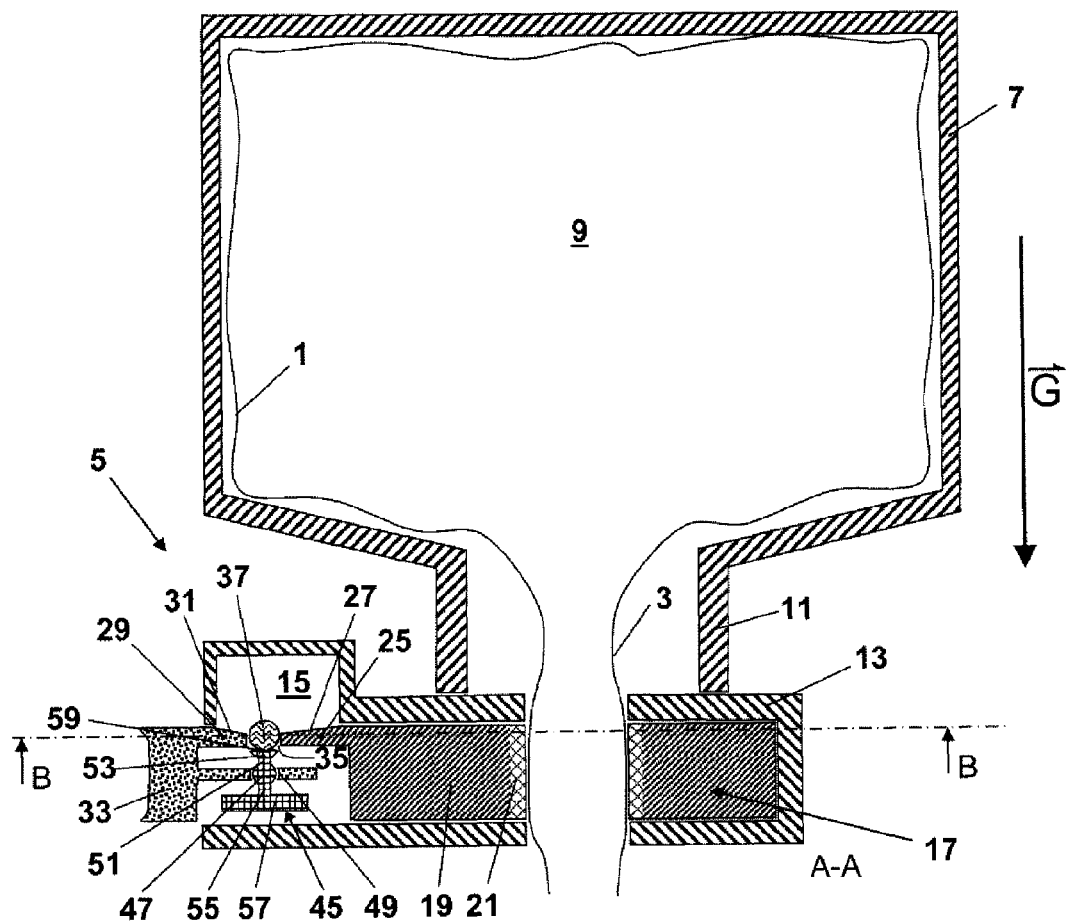
FIGS. 11a and 11b show a third preferred embodiment of an inventive valve system connected to a flexible channel of a fluid container in an upside down orientation.
Figure 11B:
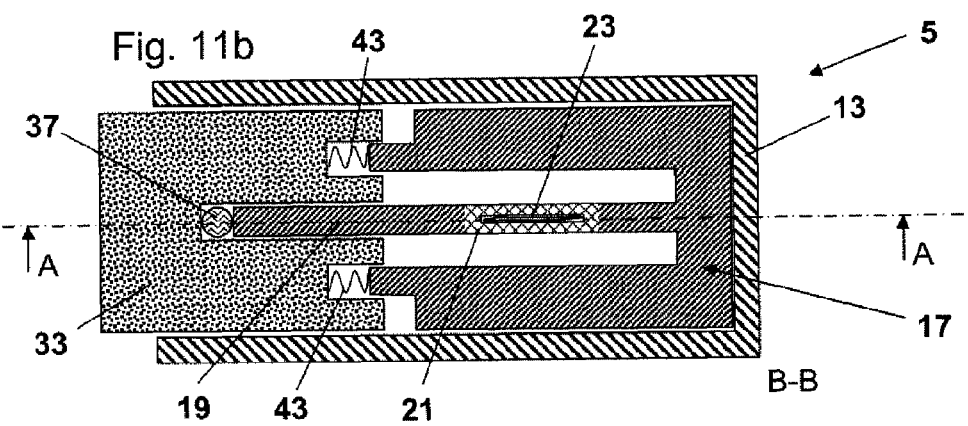

A third embodiment of the present invention is shown in FIGS. 11a, b to 14a, b. The second embodiment differs from the first by the support element which is a movably arranged pendulum 45. The pendulum 45 comprises a ball joint portion 47 with a spherical surface arranged in a ball joint socket portion 49. The ball joint socket portion 49 is a part of the actuating means 33 and located vertically below the gap 35 between the first contact portion 25 of the elongate web 19 and the second contact portion 29 of the actuating means 33. A first arm 51 of the pendulum 45 extends upwards from the ball joint portion 47 ending in a receiving portion 53. A second arm 55 of the pendulum 45 extends downwards from the ball joint portion 47 ending in a weight portion 57. The receiving portion 53 comprises a contact surface 59 shaped in the form of a spherical recess which is adapted to receive the coupling member 37 and to support it from below. The pendulum 45 is able to pivot into all radial directions within a certain range of a maximal deflection angle which is determined by the ball joint socket portion 49 or other spatial limitations.

In the upside down orientation of the container 1 shown in FIG. 11*a* the pendulum 45 has a central support position in which it is able to support the coupling member 37 in the transfer position in which the coupling member 37 is located in the gap 35 between the actuating means 33 and the closing element 19.

Figure 12A:
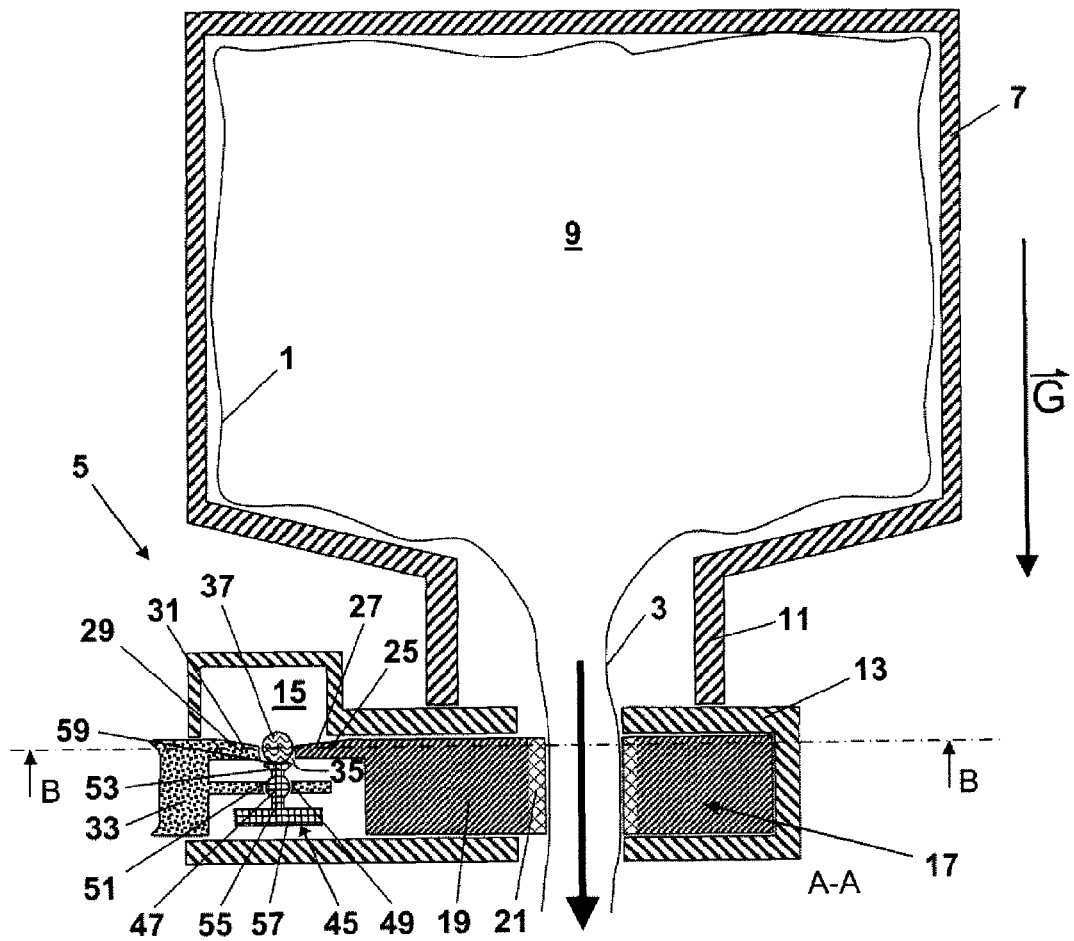
FIGS. 12a and 12b show the third preferred embodiment of an opened inventive valve system connected to a flexible channel of a fluid container in an upside down orientation.
Figure 12B:
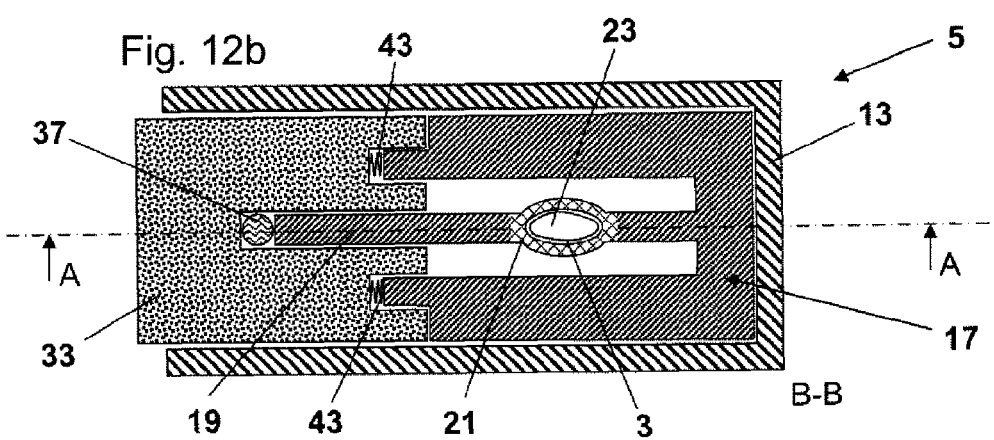

As shown in FIGS. 12*a* and 12*b* movement of the actuating means 33 is transferred by the coupling member 37 to the closing element 19 which unclamps due to the effect of the external force such that the valve system 5 opens the channel 3.

Figure 13A:
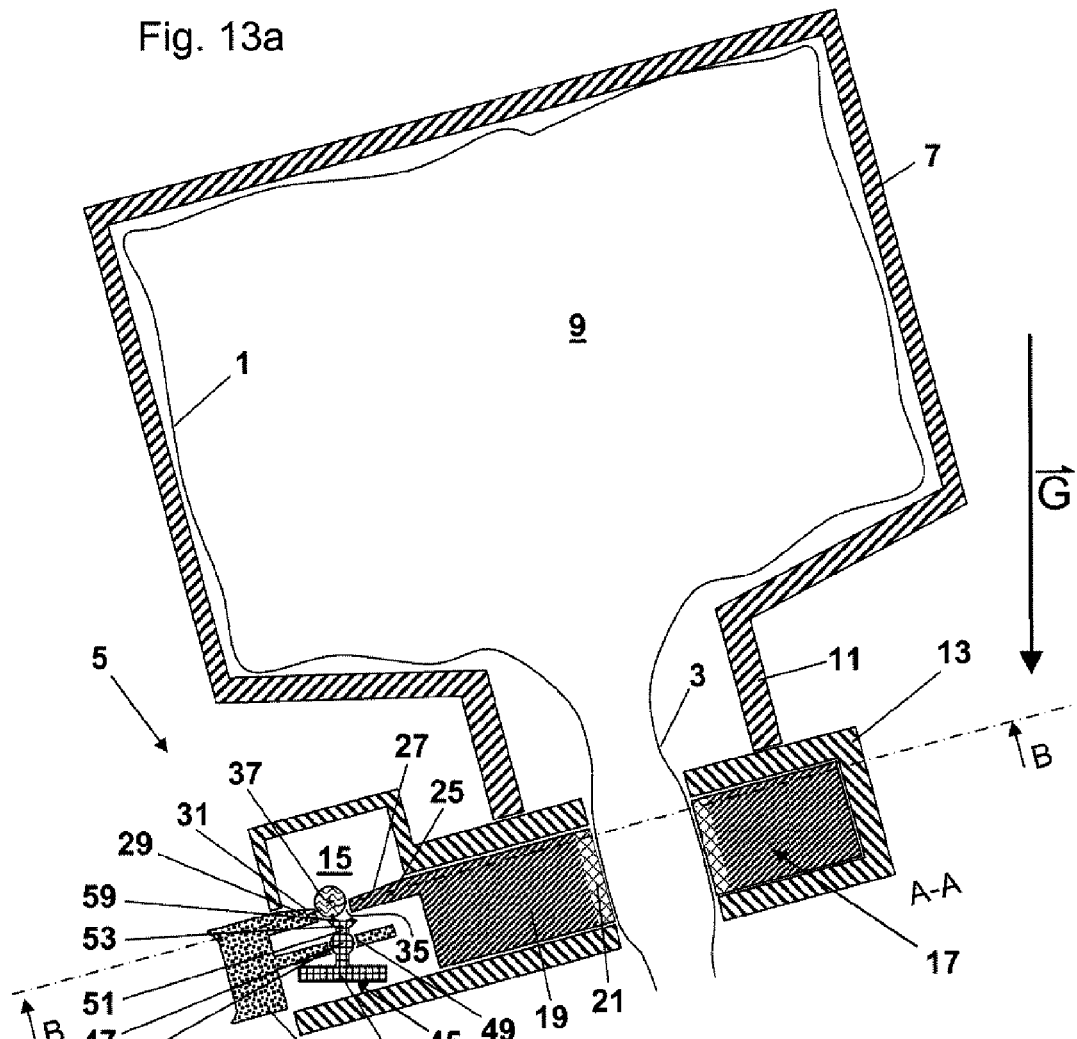
FIGS. 13a and 13b show the third preferred embodiment of a closed inventive valve system connected to a flexible channel of a fluid container having a tilted spatial orientation relative to the vertical axis.
Figure 13B:
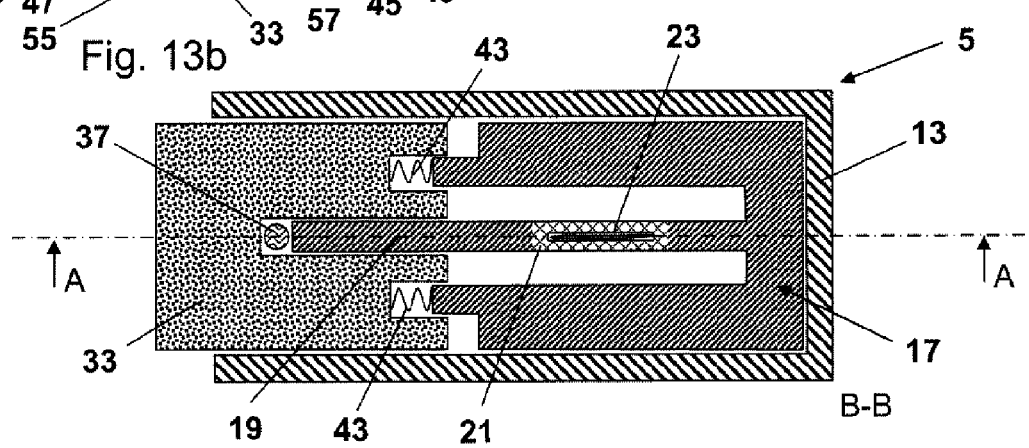
Figure 14A:
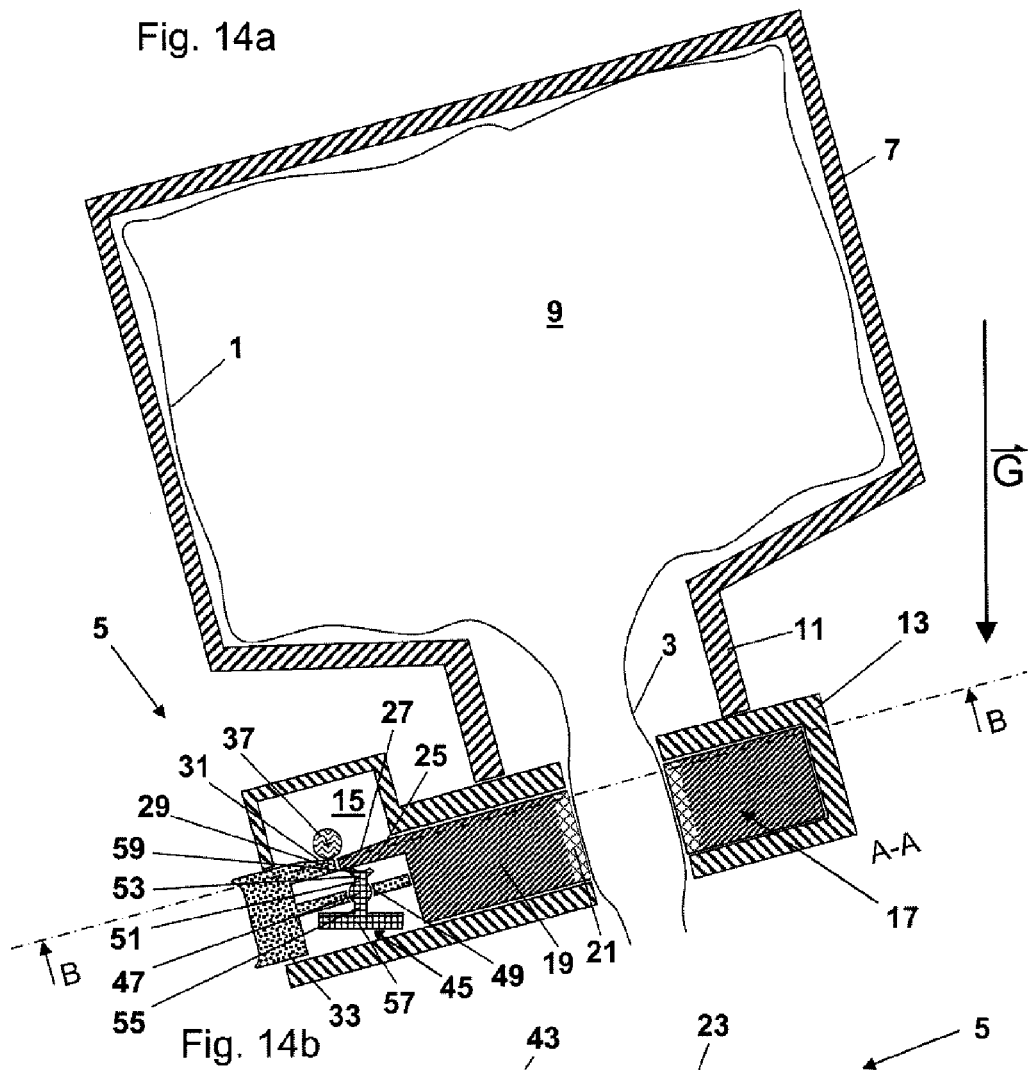
FIGS. 14a and 14b show the third preferred embodiment of a valve system according to the invention connected to a flexible channel of a fluid container having a tilted spatial orientation relative to the vertical axis, the system being in an actuated, but closed position.
Figure 14B:
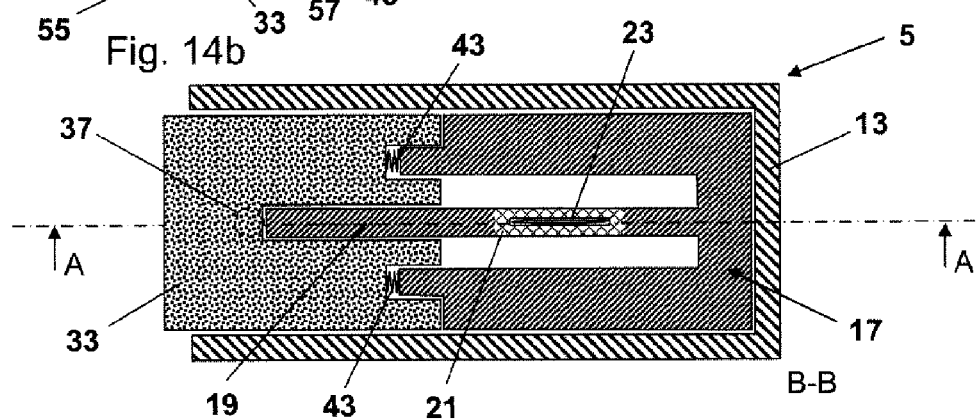

Similar to FIGS. 3*a* and 4*a*, FIGS. 13*a* and 14*a* show the fluid container 1 in a tilted spatial orientation relative to the vertical axis which is illustrated by the arrow indicating the direction of the gravitational force G. As can be seen in FIG. 13*a* the pendulum 45 keeps its vertical orientation due to the gravitational force acting on the second arm 55 ending in the weight portion 57 which is heavier than the receiving portion 53. This effect may be enhanced if the second arm 55 is chosen to be longer than the first arm 51 to make use of a leverage effect. This results in a tilt of the gap 35 with respect to the contact surface 59 of the receiving portion 53. A part of the receiving portion 53 blocks the space in the gap 35 which is needed for the coupling member 37 to keep or reach the transfer position. The coupling member 37 is therefore pushed upwards by this part of the receiving portion 53. As in the previous embodiment only less than half of the diameter of the coupling member 37 is able to protrude into the gap 35 in this tilted spatial orientation.

Similar to FIGS. 4*a* and 4*b*, FIGS. 14*a* and 14*b* show what happens if the actuating means 33 are actuated in this tilted position of the valve system 5. The coupling member 37 does not transfer the force but it is squeezed out of the gap 35, because less than half of it resides in the gap 35. Therefore, the pressing force only moves the actuating means 33 to compress the springs 43 and to reduce the gap 35 between the actuating means 33 and the closing element 17. The elongate web 19 is not upset, and the valve system 5 does not open. The valve system 5 is thereby prevented from opening in a tilted spatial orientation relative to the vertical axis. It will be appreciated that the range of tilting angles for which an opening is allowed is determined by the shape of the receiving portion 53 and the contact surface 59 on which the coupling member 37 is located when it is in the transfer position.

The invention claimed is:

1. A valve system connectable to a fluid channel (3), wherein the valve system (5) comprises an actuating means (33) and a closing element (17) for selectively closing and opening of the channel (3),
   wherein the valve system (5) comprises a chamber (15) and a movable coupling member (37), which can adapt at least two positions,
   wherein a section (48) of the coupling member (37) is located within the chamber (15) in at least one position of the coupling member (37) and the coupling member (37) is capable of moving under its gravitational force into a transfer position in which the coupling member (37) may transfer to the closing element (17) an external force acting on the actuating means (33) towards the closing element (17).

2. A valve system according to claim 1, wherein the coupling member (37) has a spherical shape and is freely movable inside the chamber (15).

3. A valve system according to claim 1, wherein the coupling member (37) protrudes with the at least one section (48) into the chamber (15) and the gravitational force is produced by the force of the weight of a movable body (44) located in the chamber (15).

4. A valve system according to claim 3, wherein the coupling member (37) is pivotably connected to the actuating means (33) and can pivot into a transfer position by the force of the weight of a movable body (44) located in the chamber (15).

5. A valve system according to claim 1, wherein the valve system (5) comprises a movably arranged support element (39, 45) which is capable of moving under its gravitational force into a support position to support the coupling member (37) from below when being in the transfer position.

6. A valve system according to claim 5, wherein the support element (39, 45) is arranged to allow the coupling member (37) to move into the transfer position only when the support element (39, 45) is in the support position.

7. A valve system according to claim 5, wherein the gravitational force on the support element (39, 45) is larger than the gravitational force on the coupling member (37) such that the support element (39, 45) is capable of pushing the coupling member (37) out of the transfer position.

8. A valve system according to claim 5, wherein the support element (39) is a spherical body (39) being movably arranged on a receiving surface (41) shaped in the form of a spherical or conical recess.

9. A valve system according to claim 5, wherein the support element (45) is a pendulum (45), wherein the pivot point of the pendulum (45), the centre of mass of the pendulum (45) and the centre of mass of the coupling member (37) are positioned on one vertical axis when the coupling member (37) is in the transfer position.

10. A valve system according to claim 9, wherein the pendulum (45) comprises a ball joint portion (47) with a spherical surface arranged in a ball joint socket portion (49) of the valve system (5), a first arm (51) extending into one direction from the ball joint portion (47) towards a receiving portion (53) of the support element (45) and a second arm (55) extending into the opposite direction from the ball joint portion (47) towards a weight portion (57) of the support element (45) wherein the receiving portion (53) is adapted to support the coupling member (37) from below.

11. A valve system according to claim 10, wherein the second arm (55) is longer than the first arm (51).

12. A valve system according to claim 1, wherein the closing element (17) is preloaded into a closing position.

13. A valve system according to claim 1, wherein the channel (3) is flexible and the closing element (17) is capable of clamping the channel (3) by a resilient force and of unclamping the channel (3) by the external force transferred to the closing element (17) via the coupling member (37).

14. A valve system according to claim 13, wherein the closing element (17) comprises an elastic portion (21) with an inner slit opening (23) such that the channel (3) is able to pass through the slit opening (23) of the elastic portion (21) of the closing element (17).

15. A valve system according to claim 14, wherein the inner slit opening (23) of the elastic portion (21) of the closing element (17) unclamps the channel (3) by expanding upon a force acting on the closing element (17) towards the channel (3) and in a transverse direction with respect to the channel (3) passing through the slit opening (23).

16. A valve system according to claim 1, wherein the actuating means (33) is spring-loaded away from the channel (3) in a transverse direction with respect to the channel (3)

providing a gap (35) between the actuating means (33) and the closing element (17) adapted to receive the coupling member (37).

17. A fluid container comprising a channel (3) for discharging the container, the channel (3) being connected to a valve system (5) according to claim 1, wherein the fluid container (1) comprises flexible material such that the inner volume is able to essentially conform with the volume of a fluid (9) contained in the container (1).

18. The fluid container according to claim 17, wherein the coupling member (37) is in the transfer position only when the fluid container (1) has a spatial orientation such that the channel (3) and the valve system (5) connected thereto are positioned below a level of a fluid (9) contained in the volume of the fluid container (1).

19. The fluid container according to claim 17, wherein the fluid container (1) is a collapsible bag comprising a flexible polymer material being framed by a rigid casing (7).

20. A valve system according to claim 6, wherein the gravitational force on the support element (39, 45) is larger than the gravitational force on the coupling member (37) such that the support element (39, 45) is capable of pushing the coupling member (37) out of the transfer position.

\* \* \* \* \*